(12) United States Patent
Babiarz et al.

(10) Patent No.: US 9,146,196 B2
(45) Date of Patent: Sep. 29, 2015

(54) AUTOMATED FILLET INSPECTION SYSTEM WITH CLOSED LOOP FEEDBACK AND METHODS OF USE

(75) Inventors: Alec Babiarz, Encinitas, CA (US); Stephane Etienne, Bouaye (FR); Owen Yikon Sit, Ladera Ranch, CA (US)

(73) Assignee: Nordson Corporation, Westlake, OH (US)

( * ) Notice: Subject to any disclaimer, the term of this patent is extended or adjusted under 35 U.S.C. 154(b) by 933 days.

(21) Appl. No.: 12/936,643

(22) PCT Filed: Jul. 9, 2009

(86) PCT No.: PCT/US2009/050067
§ 371 (c)(1),
(2), (4) Date: Nov. 30, 2010

(87) PCT Pub. No.: WO2010/006141
PCT Pub. Date: Jan. 14, 2010

(65) Prior Publication Data
US 2011/0063606 A1 Mar. 17, 2011

Related U.S. Application Data

(60) Provisional application No. 61/079,547, filed on Jul. 10, 2008.

(51) Int. Cl.
*G06K 9/00* (2006.01)
*G01N 21/95* (2006.01)

(52) U.S. Cl.
CPC .................................... *G01N 21/95* (2013.01)

(58) Field of Classification Search
CPC ....... G01N 21/00; G01N 21/88; G01N 11/00; G06K 9/00; B05D 1/02; B05D 5/12
See application file for complete search history.

(56) References Cited

U.S. PATENT DOCUMENTS

RE35,423 E  1/1997 Adams et al.
6,321,591 B1 * 11/2001 Breunsbach et al. ........ 73/53.01
(Continued)

FOREIGN PATENT DOCUMENTS

JP  2002139452 A  5/2002
JP  2007194403 A  8/2007

OTHER PUBLICATIONS

The State Intellectual Property Office of the People's Republic of China, First Office Action received in related Chinese application No. 200980119456.7 dated Jul. 12, 2012.
Commissioner for Patents, International Search Report issued in related international application No. PCT/US09/50067 dated Aug. 10, 2009.
The International Bureau of WIPO, International Preliminary Report on Patentability issued in related international application No. PCT/US2009/050067 dated Jan. 11, 2011.
(Continued)

*Primary Examiner* — John Strege
(74) *Attorney, Agent, or Firm* — Wood, Herron & Evans, LLP

(57) ABSTRACT

Systems and methods for automated inspection of fillet formation along on or more peripheral edges (13a) of a packaged microelectronic device (14) that is attached to a supporting substrate (16), such system (10) including a feedback loop for controlling fillet formation More specifically, the system (10) includes a dispensing system (18) configured for dispensing underfill material (22) onto the supporting substrate (16) The system (19) further includes an automated optical inspection (AOI) system (19) configured for determining a value of a measurable attribute of the fillet (12), such as whether the fillet (12) is properly dimensioned, i e, sized and shaped A feedback loop (66) is included between the dispensing system (18) and automated optical inspection system (19).

14 Claims, 3 Drawing Sheets

(56) References Cited

U.S. PATENT DOCUMENTS

| | | | |
|---|---|---|---|
| 6,567,161 B1* | 5/2003 | Lee | 356/237.1 |
| 6,621,566 B1* | 9/2003 | Aldrich et al. | 356/237.1 |
| 7,171,897 B2 | 2/2007 | Barajas et al. | |
| 7,622,311 B1* | 11/2009 | Cha et al. | 438/16 |
| 2004/0148763 A1 | 8/2004 | Peacock et al. | |
| 2004/0148876 A1 | 8/2004 | McManus et al. | |
| 2004/0175832 A1* | 9/2004 | Hui et al. | 436/8 |
| 2005/0095366 A1 | 5/2005 | Fang et al. | |
| 2005/0134842 A1* | 6/2005 | Savareigo et al. | 356/237.5 |
| 2007/0182018 A1* | 8/2007 | Pendse | 257/777 |
| 2008/0038870 A1* | 2/2008 | Gupta et al. | 438/108 |
| 2008/0040058 A1* | 2/2008 | Fujii et al. | 702/81 |
| 2008/0105703 A1 | 5/2008 | Prentice et al. | |

OTHER PUBLICATIONS

Japanese Patent Office, Office Action issued in Japanese Patent Application No. 2011-517608 dated Aug. 7, 2013.

The State Intellectual Property Office of the People's Republic of China, Office Action issued in application No. 200980119456.7 dated Dec. 10, 2013.

The State Intellectual Property Office of the People's Republic of China, translation of Official Action issued in application No. 200980119456.7 dated Jun. 13, 2014.

Japanese Patent Office, translation of Official Action issued in Japanese Patent Application No. 2011-517608 dated Aug. 25, 2014.

\* cited by examiner

AUTOMATED FILLET INSPECTION SYSTEM WITH CLOSED LOOP FEEDBACK AND METHODS OF USE

CROSS-REFERENCE TO RELATED APPLICATIONS

This application claims the benefit of U.S. Provisional Application No. 61/079,547, filed Jul. 10, 2008, the disclosure of which is hereby incorporated by reference herein in its entirety.

BACKGROUND

The present invention relates generally to an automated system for inspecting and controlling fillet formation, and more specifically to a system and method for inspection of fillet formation along an edge(s) of a packaged microelectronic device, which is attached to a supporting substrate.

In the semiconductor industry, fillet may be found along one or more edges, including corners, of a packaged microelectronic device, e.g., a ball grid array (BGA), chip scale package (CSP), or flip chip, which is attached to a supporting substrate, e.g., a printed circuit board (PCB), via known dispensing processes. The fillet is an attribute of an underfill material that is incorporated into the assembly of the packaged microelectronic device and supporting substrate to add strength to the mechanical connections and to protect against environmental damage.

In one example, a defined amount of a curable underfill material, such as an epoxy, is dispensed from a dispensing device along one or more edges of a rectangular-shaped packaged microelectronic device, which has been previously soldered with solder bump interconnections or another type of attachment to a PCB. By capillary action, the material is drawn into the gap underneath the packaged microelectronic device and, as it flows outward to the other edges of the packaged microelectronic device, underfills the packaged microelectronic device, i.e., fills the gap between the packaged microelectronic device and the PCB. The fillet is formed around the packaged microelectronic device, which extends from the sides of the packaged microelectronic device to the PCB. In other words, the fillet is not under the packaged microelectronic device but forms along the edges of the packaged microelectronic device. The underfill material is eventually cured, typically thermally cured by heating, after fillet formation. The fillet may be uniform, or not, and may be further enhanced by a secondary dispensing process known in the art as a "seal pass".

In another example, the dispensing process utilizes edge or corner bond dispensing of curable underfill material to form fillets known in the art, respectively, as edge bonds or corner bonds. In this process, the fillet is directly formed along one or more, or a portion of, the edges, including the corners, of the packaged microelectronic device, without underfilling the space between the packaged microelectronic device and supporting substrate. With corner bond dispensing, the dispensed material may only partially flow under the packaged microelectronic device to provide bonding. Again, the underfill material is eventually cured after fillet formation.

A fluxing or "no-flow" underfill process is yet another technique for forming fillets. In this process, underfill material is first dispensed on a supporting substrate's solder pads, then a packaged microelectronic device is placed on top of the underfill material. As the packaged microelectronic device is forced down onto the corresponding solder pads, the packaged microelectronic device displaces the underfill material. Excess material forms a fillet along the edges of the packaged microelectronic device. This assembly is then put through an oven that reflows the solder to attach the packaged microelectronic device to the supporting substrate and cure the underfill material at the same time.

The resulting assembly may be subjected to shock, vibration, thermal cycling, or other environmental stresses in its intended use. The underfill material, which includes the corner bond material, in each of the above processes helps improve the reliability and operational longevity of the resulting assembly.

Numerous variables that can affect fillet formation. The variables can include, for example, the viscosity, surface tension, volume, and/or temperature of the underfill material, as well as the surface characteristics and temperature of the packaged microelectronic device and supporting substrate. Those variables can be inter-dependent, e.g., temperature affects viscosity, and/or dynamic, i.e., change over time. Because precise control of the variables can be difficult to obtain, quality and consistency of the underfill dispensing process, likewise, can be difficult to achieve, as well as sustain once so achieved.

Conventional methods of monitoring fillet formation involve human inspection of the resulting fillet. For example, in one instance, the human inspector simply observes the size and shape of the fillet formed along the edge(s) of the packaged microelectronic device that is attached to the supporting substrate to determine whether the fillet is properly dimensioned. If the fillet is improperly dimensioned, the operating parameters of the underfill dispensing process, e.g., the temperature of the supporting substrate or amount of the underfill material, can be adjusted accordingly to change the fillet size and/or shape. Unfortunately, manual inspection exhibits numerous limitations. For example, the subjectivity of evaluating whether the fillet is properly dimensioned varies from operator to operator. In addition, traceability make be lacking for the manual inspection process.

It would thus be beneficial to provide an improved system and method for inspecting and controlling fillet formation that overcomes the aforementioned drawbacks.

SUMMARY

In one embodiment, an automated system is provided for use in analyzing a material dispensed onto a supporting substrate. The system includes a dispensing system and an automated optical inspection system. The dispensing system has a dispensing device configured to dispense the material onto the supporting substrate. The automated optical inspection system is configured to capture an image of the material and to analyze the image to determine a value of a measurable property of the dispensed material. A feedback loop couples the automated optical inspection system with the dispensing system. The automated optical inspection system is configured to communicate the value of the measurable property of the material dispensed at the peripheral edge of the gap over the feedback loop to the dispensing system.

In another embodiment, a method is provided for use in analyzing a material dispensed onto a supporting substrate. The method includes dispensing the material onto the supporting substrate and then transferring the supporting substrate and the dispensed material from the dispensing system to an automated optical inspection system. The automated optical inspection system is used to determine a value of a measurable property of the dispensed material, which is communicated from the automated optical inspection system to the dispensing system.

BRIEF DESCRIPTION OF THE DRAWINGS

The accompanying drawings, which are incorporated in and constitute a part of this specification, illustrate embodiments of the invention and, together with a general description of the invention given above, and the detailed description of the embodiments given below, serve to explain the principles of the invention.

DETAILED DESCRIPTION

Figure 1:
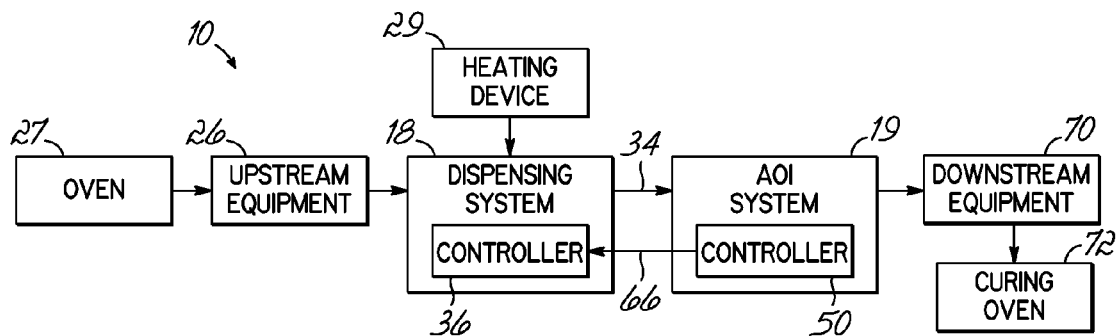
FIG. 1 is a diagrammatic view of an automated system for inspecting and controlling fillet formation in accordance with an embodiment of the invention.

With reference to FIGS. 1-4 and in accordance with an embodiment of the invention, an automated system 10 is configured to inspect and control the formation of a fillet 12. A packaged microelectronic device 14 is directly mounted to a supporting substrate 16. The fillet 12 is formed along one or more peripheral edges 13a and 13b of the packaged microelectronic device 14 via a dispensing process, e.g., an underfill dispensing process, as described below. In one example, the packaged microelectronic device 14 can be a surface mount package such as a ball grid array (BGA), a chip scale package (CSP), or a flip chip, and the supporting substrate 16 may be a printed circuit board (PCB). The packaged microelectronic device 14 can include one or more semiconductor chips or die, an interposer substrate or lead frame attached to the die, a molded outer casing encapsulating the die, and external connections for coupling the die with the supporting substrate 16. The packaging of the packaged microelectronic device 14 protects the die from environmental and handling hazards and permits the die inside the packaged microelectronic device 14 to be electrically and mechanically attached to the supporting substrate 16.

In the representative embodiment, the automated system 10 includes dispensing system 18 that performs an underfill dispensing process. The dispensing system 18 includes a controller 36 and a dispensing device 21 that operates under the control of control signals supplied by the controller 36.

The dispensing device 21 includes a dispensing nozzle 20 (shown in partial) used to dispense an underfill material 22 that may infiltrate and fill a gap 24 between the packaged microelectronic device 14 and the supporting substrate 16 by capillary action.

In one embodiment, the dispensing device used in the dispensing system 18 may be a "jetting" dispenser commonly used in the electronics industry to selectively dispense small amounts or droplets of a highly fluid material in a non-contact manner onto a substrate like supporting substrate 16. One type of jetting dispenser includes a valve seat surrounding a discharge passage and a needle having a tip that is configured to move relative to the valve seat. When the tip of the needle is in contact with the valve seat, the discharge passage is isolated from a chamber supplied with pressurized fluid material. To dispense droplets of the fluid material from the jetting dispenser in dispensing system 18, the tip of the needle is lifted from the valve seat so that a small amount of the fluid material flow from the chamber through the valve seat to the discharge passage. The tip of the needle is then moved rapidly toward the valve seat to close the flow path and transfer momentum to the fluid material in the discharge passage causes a droplet of the material to be ejected, or "jetted," from an outlet of the discharge passage. The droplet, which contains a small discrete volume of the fluid material, travels with a ballistic trajectory and eventually lands at a specified location on the circuit board.

The jetting dispenser of the dispensing system 18 is configured to "fly" above the supporting substrate 16 at a fixed height and to jet the material onto an intended application area in a non-contact manner. To that end, the jetting dispenser of the dispensing system is typically moved by a robot (not shown) in a pattern across a surface of the supporting substrate 16. By rapidly jetting the material "on the fly" (i.e., while the jetting dispenser is in motion) under the control of controller 36, the dispensed droplets may be joined to form a continuous line. Consequently, such jetting dispensers may be readily programmed for use in the dispensing system 18 to dispense desired patterns of a fluid material, such as underfill.

Figure 2:
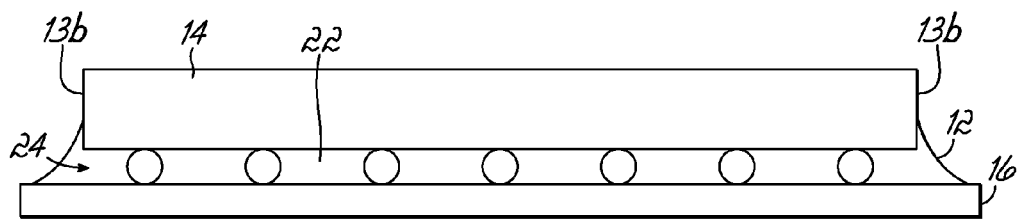
FIG. 2 is a side elevation view of a packaged microelectronic device and supporting substrate showing the packaged microelectronic device attached thereto.

Prior to receipt for processing by the automated system 10, the packaged microelectronic device 14 and supporting substrate 16 are pre-assembled, e.g., soldered together, thereby forming gap 24 therebetween, as best shown in FIG. 2. In one embodiment, the packaged microelectronic device 14 is attached to the supporting substrate 16 by bumping the packaged microelectronic device 14 with solder bump interconnections. To bump the chip, the bottom surface of the packaged microelectronic device 14 can be coated with regions of underbump metal (UBM) to enhance the electrical connection, to protect the packaged microelectronic device 14 from the bump materials, and to define the bump size and location. The solder bump interconnections, which mechanically attach the packaged microelectronic device 14 to the supporting substrate 16, also provide electrically conductive paths for power and signals and thermally conductive paths to dissipate heat generated when the packaged microelectronic device 14 is operating. Heating the assembly of the packaged microelectronic device 14 and supporting substrate 16 in an oven 27, e.g., a reflow oven, melts the solder, which acts to connect the packaged microelectronic device 14 and the supporting substrate 16 when solidified.

The assembly consisting of the packaged microelectronic device 14 and supporting substrate 16 is fed into dispensing system 18 from suitable upstream equipment 26. The upstream equipment 26 can include a loader known in the art, such as an in-line conveyer system or an automated loader that transfers or feeds the packaged microelectronic device 14 and supporting substrate 16 into the dispensing system 18 via cassettes containing the packaged microelectronic device 14 and supporting substrate 16. Alternatively, the upstream equipment 26 may include the oven 27, as well as the loader.

Once situated within the dispensing system 18, the pre-assembled packaged microelectronic device 14 and/or supporting substrate 16 can be pre-heated via a heating device 29, as known to a person having ordinary skill in the art. After pre-heating, the position of the assembly in the dispensing system 18 may be evaluated before dispensing the underfill material 22. Alternatively, the assembly of the packaged microelectronic device 14 and supporting substrate 16 may be pre-heated in the oven 27.

Figure 3:
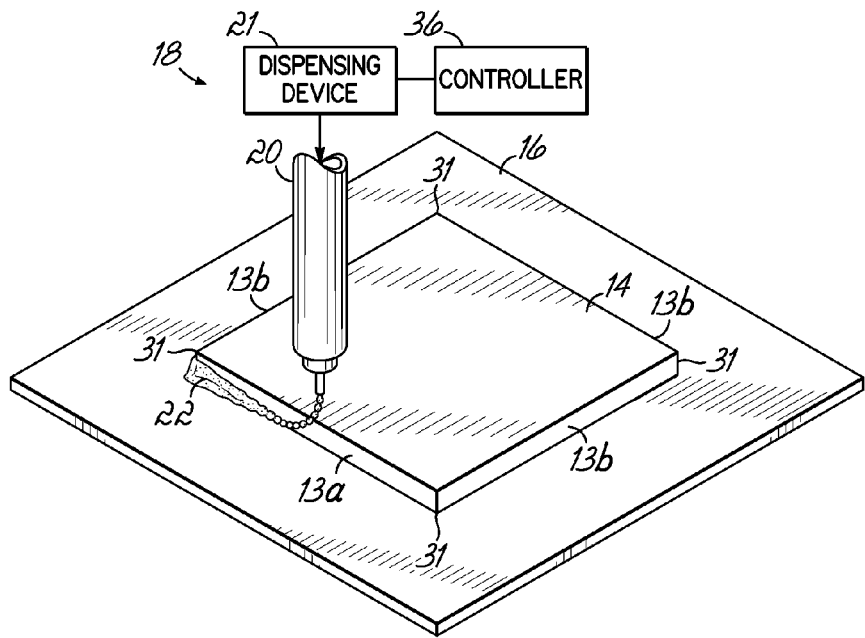
FIG. 3 is a perspective view of a portion of a dispensing device dispensing material along an edge of the packaged microelectronic device of FIG. 2 via an underfill dispensing process so as to form a fillet.
Figure 4:
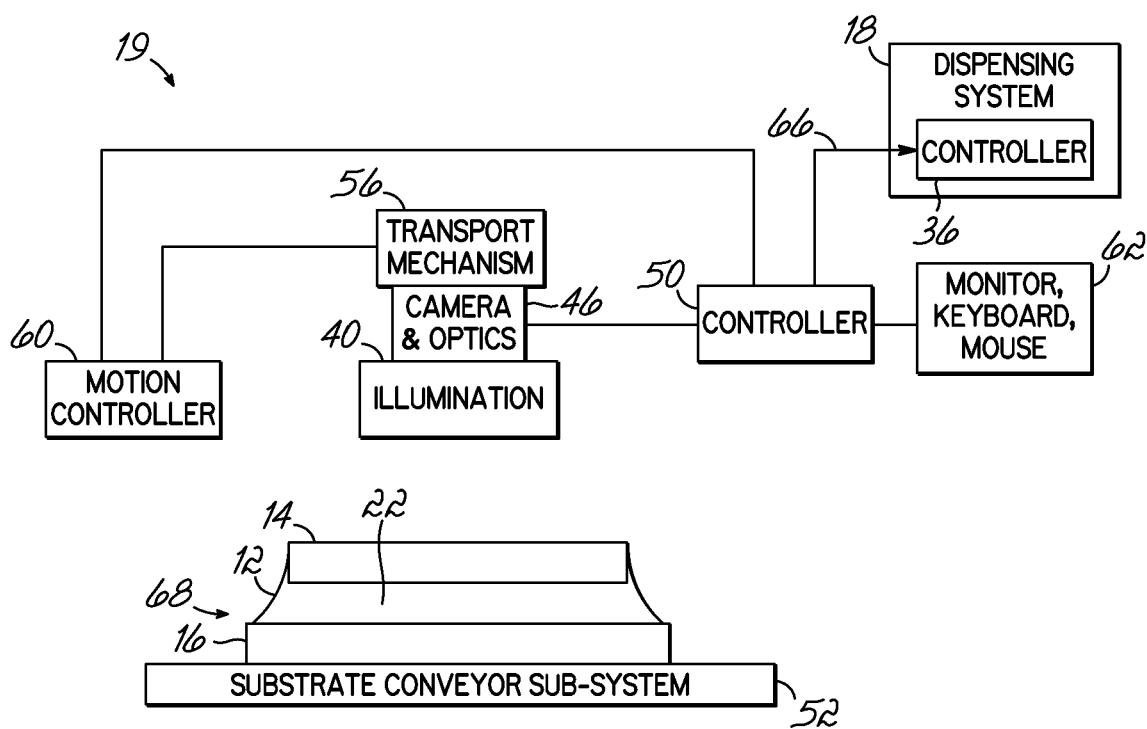
FIG. 4 is a diagrammatic view of the automated optical inspection system of FIG. 1 used to inspect the fillet formed as in FIG. 3 and interfaced with the dispensing system in accordance with an embodiment of the invention.

As shown in FIG. 3, the underfill material 22 is dispensed from the dispensing device 21 along at least one of the peripheral edges 13a of the packaged microelectronic device 14 so as to fill the gap 24 (FIG. 2) by capillary flow and, thus, form the fillet 12 (FIG. 4). The peripheral edges 13a at which dispensing is performed under the control of controller 36 may be referred to as the dispensing peripheral edges. As earlier explained, by capillary action, the dispensed material 22 is drawn underneath the packaged microelectronic device 14 and fills the gap 24 as it flows outward to the non-dispensing peripheral edge(s) 13b, or flow-out edges, of the packaged microelectronic device 14. A single pass or multiple passes may occur along dispensing peripheral edge 13a, which may define an I-shape. Dispensing also may occur along multiple peripheral edges 13a, 13b so as to define an L-pass shape, for example. In addition, after the gap 24 has been filled, an optional seal pass (not shown) may be applied around the material 22 at the dispensing peripheral edges 13b so as to finish the fillet 12 (FIG. 4). Any material suitable for filling the gap and forming the fillet 12 may be utilized. In one example, the underfill material 22 is a curable non-conductive polymeric material such as an epoxy. The underfill material 22 may comprise one or more polymerizable monomers, polyurethane prepolymers, block copolymers, and radial copolymers, as well as substances like initiators, catalysts, cross-linking agents, stabilizers, and the like. When cured and hardened, such polymeric materials 22 contain molecules that are chained or cross-linked to form a strongly bonded mass.

Alternatively, the dispensing system 18 may also provide corner or edge bond dispensing wherein the material 22 only forms fillet 12 at peripheral edge 13a, or one or more corners 31, without underfilling the gap 24 beneath the packaged microelectronic device 14. In the case of corner or edge bond dispensing, the dispensing of the material 22 can occur along one or more of the edges 13a, 13b, or corners 31, or a portion thereof to form fillet 12. And, with corner bond dispensing, the packaged microelectronic device 14, as shown in FIG. 3B, may have one or more corner bonds 28 and no fillet formation.

After the material 22 has been dispensed, the packaged microelectronic device 14 and supporting substrate 16 carrying the material 22 forming fillet 12 may be heated via a heating device so that the material 22 can jellify. Jellification helps stabilize the material 22 so that the packaged microelectronic device 14 and supporting substrate 16 can be handled before evaluation at the AOI system 19. In some cases, the stability of the material 22 may suffice for inspection such that the material 22 does not have to be first jellified.

Figure 1A:
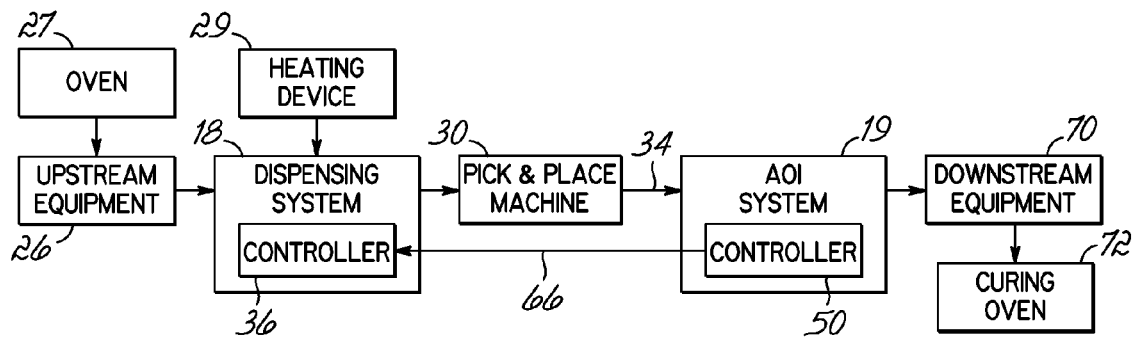
FIG. 1A is a diagrammatic view similar to FIG. 1 of an automated system for inspecting and controlling fillet formation in accordance with another embodiment of the invention.
Figure 3A:
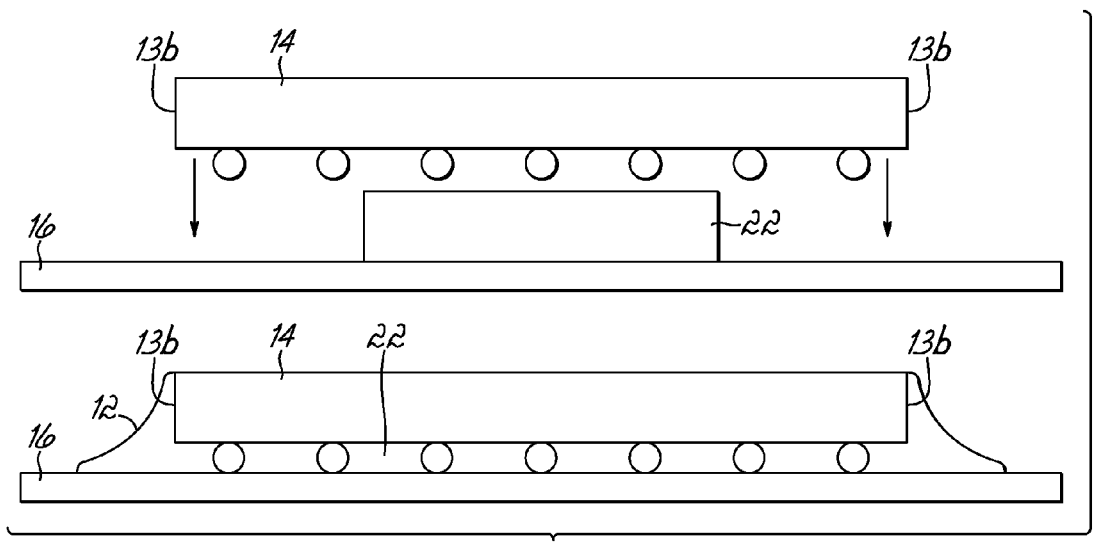
FIG. 3A is a side elevation view illustrating fillet formation in a no-flow dispensing process.
Figure 3B:
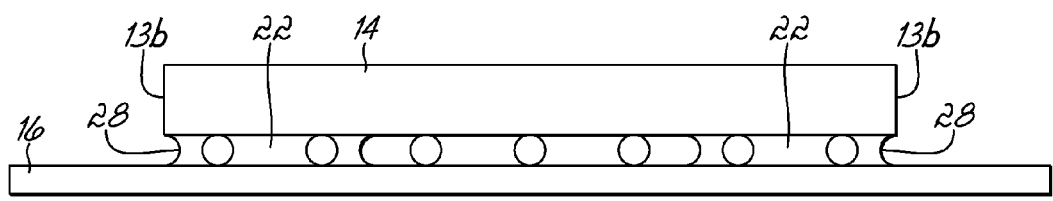
FIG. 3B is an enlarged view of a semiconductor and supporting substrate assembly showing a corner bond with no fillet formation formed via corner bond dispensing.

With reference to FIGS. 1A and 3A in which like reference numerals refer to like features in FIGS. 1-3 and in accordance with an alternative embodiment, the dispensing system 18 of the automated system 10 is configured to utilize a no-flow underfill dispensing process. The dispensing system 18 includes a dispensing device similar to dispensing device 21 that dispenses the material 22 onto solder pads (not shown) of the supporting substrate 16. The material 22 for the no-flow process generally includes fluxing and epoxy characteristics. After dispensing, the supporting substrate 16 with material 22 is transported, such as via a conveyor assembly, from the dispensing system 18 to the pick and place machine 30. At the pick and place machine 30, the packaged microelectronic device 14 is placed on top of the underfill material 22. Any suitable pick and place machine 30, as is known to a person having ordinary skill in the art, may be utilized to perform this operation. The packaged microelectronic device 14 displaces the material 22 as the packaged microelectronic device 14 is forced down onto the supporting substrate 16 by the pick and place machine 30. The excess displaced material forms the fillet 12 along the edges 13b of the packaged microelectronic device 14. The assembly of packaged microelectronic device 14 and supporting substrate 16 with fillet 12 is then transported from the pick and place machine 30 to the AOI system 19, as further described below.

Figure 1B:
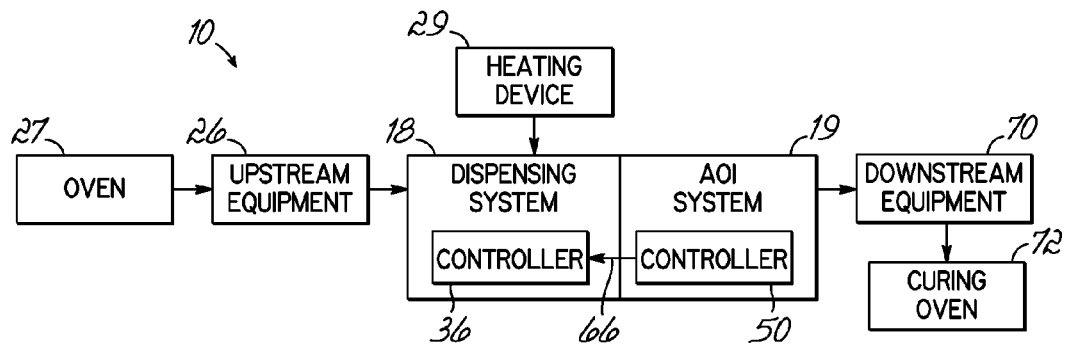
FIG. 1B is a diagrammatic view similar to FIGS. 1 and 1A of an automated system for inspecting and controlling fillet formation in accordance with yet another embodiment of the invention.

With reference to FIG. 1B in which like reference numerals refer to like features in FIGS. 1-3 and in accordance with an alternative embodiment, the dispensing system 18 and the AOI system 19 of the automated system 10 may be combined into a single chassis. In this combined machine format, the controllers 36, 50 are linked by the feedback loop 66, as further described below. In certain embodiments, the controllers 36, 50 may be merged into a single controller that has the functionality of the individual controllers. In this instance, the assembly of the packaged microelectronic device 14, supporting substrate 16, and material 22 may be transported internally to the chassis from a location suitable for dispensing the material 22 to a different location suitable for inspecting the dispensed material 22, or the dispensing and inspection location may be shared such that the assembly is stationary during these operations or merely moved over a minor distance to accommodate accurate dispensing and imaging.

As one example of a suitable dispensing system 18, the Axiom series, such as the Axiom X-1020 Dispensing System, available from Asymtek of Carlsbad, Calif., may be utilized in embodiments of the present invention.

As earlier mentioned, a number of variables that can affect the fillet 12 (FIG. 4) formed from the dispensing process can include, for example, the viscosity, surface tension, volume, and/or temperature of the material 22, as well as the surface characteristics or temperature of the packaged microelectronic device 14 and supporting substrate 16. The dispensing system 18 generally includes one or more software features capable of controlling certain of the various variables, e.g., volume or amount dispensed and temperature of the supporting substrate, and consequently underfill material 22 after it is dispensed. So as to yield properly dimensioned fillets 12, operating parameters for the underfill dispensing system 18 are defined that take into consideration the different variables that can affect the fillet 12, as well as the desired size and shape, e.g., length, width, and height, of the fillet 12. With operating parameters established, the AOI system 19, which is further discussed below, provides automated analysis of the fillet 12 so that those operating parameters can be monitored and the proper dimensions of the fillet 12 maintained. As a result, the quality and consistency of the underfill dispensing process may be maintained in real-time. In particular, the AOI system 19 can send, or feed, information directly back to the dispensing system 18 and the dispensing software can adjust the dispensing parameters, such as volume of material 22, to correct the size of the fillet 12.

With further reference to FIGS. 1, 1A, 3, 3A, and 4, the packaged microelectronic device 14 and supporting substrate 16 with fillet 12 next move directly from the underfill dispensing system 18, or directly from the pick and place machine 30 in the case of no-flow dispensing, to the AOI system 19, which is configured for determining whether the fillet 12 is properly dimensioned. The systems 10 of FIGS. 1 and 1A may define an "island of automation" or an inline system, as are known in the art. Generally, an island of automation represents a single robotic system, or other automatically operating machine, that functions independently of any other machine or process. An inline system is an arrangement of equipment in which the product being assembled passes consecutively from operation to operation until completed. Accordingly, the AOI system 19 and dispensing system 18 may be contained in the island of automation, or alternately, the AOI system 19 and dispensing system 18 may be considered to be arranged inline relative to each other. In either the inline or island of automation arrangement, the AOI system 19 of FIGS. 1 and 1A may be configured to transport the assembly of packaged microelectronic device 14 and supporting substrate 16 with fillet 12 from the dispensing system 18 or pick and place machine 30, respectively, via a substrate conveyer sub-assembly 34. Alternatively, the dispensing system 18, or pick and place machine 30, may utilize loaders (not shown) and unloaders (not shown) to pass cassettes, which include the packaged microelectronic device 14 and supporting substrates 16 with fillets 12, to the AOI system 19.

With specific reference now to FIG. 4, the AOI system 19 generally includes a lighting sub-system 40 having at least one light source that directs visible light, e.g., white and/or multi-color light, onto the fillet 12 to produce a natural image thereof. The lighting sub-system 40 is able to illuminate the fillet 12 under computer control. The light source can be used in fiducial alignment, barcode reading, or optical character recognition (OCR) of the device. Barcode or OCR may be desirable to provide traceability for the process.

The AOI system 19 further includes a camera sub-system 46, which has at least one camera with optics, e.g., a lens, positioned to capture one or more images of the fillet 12 when light is emitted thereon from the lighting sub-system 40. The camera 46 is depicted in the representative embodiment as being situated directly above the packaged microelectronic device 14 to capture one or more images of the fillet 12. However, it should be understood that more than one camera 46 may be provided at various positions to capture images of the fillet 12, including the various edges 13a, 13b thereof. The captured images are conveyed to a controller 50, which may have the representative form of an image-processing computer, for determining the size and shape of the fillet 12, i.e., whether the fillet 12 is properly dimensioned. The size and shape of the fillet 12 are compared against targeted or predetermined values of size and shape as a standard to determine whether the underfill dispensing system 18 is operating effectively and whether any of the operating parameters thereof need to be adjusted.

The AOI system 19 also includes the substrate conveyor sub-system 52, for conveying the supporting substrate 16 from the dispensing system 18 (or pick and place machine 30) and holding the supporting substrate 16 during inspection of the fillet 12. In place of the substrate conveyor sub-system, a loader (not shown) may be utilized to place the packaged microelectronic device 14 and supporting substrate 16 with fillet 12 onto a substrate holder sub-system (not shown). The substrate holder sub-system can support the supporting substrate 16 from below by using support pins, for example, configured to securely situate the supporting substrate 16.

A transport mechanism 56, which can also be included as part of the AOI system 19, includes an XY-axis motor, which is connected to and moves the camera to aid in inspection of the fillet 12. Other options are contemplated including but not limited to incorporation of Z-axis movement, as desired.

The controller 50 of the AOI system 19 is coupled with the camera sub-system 46, as well as with a motion controller 60 for providing movement commands to the XY motor of the transport system 56. The coupling may rely on optical signals or electrical signals to, for example, communicate a representation of an image from the camera of the camera sub-system 46 to the controller 50. The controller 50 includes one or more software programs capable of executing machine vision algorithms for evaluating the shape and size of the fillet 12 as depicted in the captured images. A user interface with the AOI system 19 may be include a computer monitor, keyboard, and/or mouse, depicted generally as reference numeral 62, which are operatively linked with the controller 50.

One such AOI system 19 that may be utilized to perform automated inspection of the fillet 12 is the YTV Series AOI, such as the F or M Series, available from YESTech Inc. of San Clemente, Calif.

The inspection program for the AOI system 19 generally starts with a properly dimensioned fillet as a comparative standard. The fillet dimensions may be manually entered into the AOI system 19 or the fillet 12 can be automatically inspected by the AOI system 19 so that the image-processing software can train itself. Once the fillet dimensions are input and/or the learning process has been accomplished, automated inspection of fillets 12 can occur within the AOI system 19. Fiducial alignment is typically performed as part of the inspection process. In addition, the inspection process may be many times faster than the dispensing process. For example, inspection speed may be around 1 square inch per second, and 20 to 30 seconds for the fillet 12, whereas dispensing of the fillet material 22 for the fillet 12 may take up to 5 minutes. Thus, in one representative embodiment, the entire fillet, e.g., all four edges 13a, 13b of the fillet 12, may be completely inspected. In another representative embodiment, only the shape and size of the fillet 12 at one or more of the flow-out edges 13b is inspected.

The automated system 10 includes a feedback loop 66 for closed loop control of a dispensing system 18 by measurements made by an automated optical inspection (AOI) system 19. The feedback loop 66 promotes control over fillet formation at the dispensing system 18, i.e., maintain a desired size and shape of the fillet 12. The feedback loop 66 associates, or connects, the controller 36 at the dispensing system 18 and the controller 50 at the AOI system 19 so that information can be bidirectionally exchanged between the AOI system 19 to the dispensing system 18 or unidirectionally communicated from the AOI system 19 to the dispensing system 18. The exchanged or communicated information may be, for example, values of a measurable property of the fillet material 22, such as shape, dimensions, or another attribute, determined at the AOI system 19. The values of the measurable property are typically numerical but, in an alternative embodiment, may be qualitative.

Suitable interfacing to provide the feedback loop 66 may be accomplished by networking the two systems 18, 19 using known techniques. The feedback loop 66 coupling the controller 36 at the dispensing system 18 with the controller 50 at the AOI system 19 may include a communications link, e.g., a cable, and an algorithm executing on the dispensing system 18 to facilitate operating parameter adjustment. In another embodiment, the feedback loop 66 may be defined by a human operator (not shown) at the dispensing system 18 who manually attends to adjusting operating parameters of the underfill dispensing system 18 based upon fillet information obtained from the AOI system 19.

In response to the value of the measureable property communicated over the feedback loop 66, the dispensing system 18 is configured to adjust one or more operating parameters to allow proper dimensioning of the fillet 12 to be maintained. This communication and adjustment supplies the closed loop feedback of a closed-loop control system between the AOI system 19 and the dispensing system 18. In such a closed-loop control system, the values of the measureable property of the fillet 12 are fed from the controller 50 of the AOI system 19 as a reference to the controller 36 of the dispensing system 18, which continuously or intermittently adjusts the control input to the material dispensing operation at the dispensing system 18 as necessary to minimize or regulate the control error. Alternatively, the AOI system 19 may determine the adjustment from the measurable attribute and communicate the adjustment to the dispensing system 18. Based on the feedback from the AOI system 19 of the actual performance of the dispensing system 18, the dispensing system 18 may dynamically compensate for disturbances to the control system that cause changes to the fillet 12, such as changes in shape or dimensions, or that may result in the unwanted formation of a fillet. One objective of the control system is to maintain the controlled process of dispensing the fillet 12 within an acceptable operating range.

For example, if the fillet 12 is determined to be improperly dimensioned by the AOI system 19, the operating parameters of the dispensing system 18 can be adjusted accordingly via the information communicated to the dispensing system 18 over the feedback loop 66. In one specific example, in response to detecting an abnormally small fillet size, that information can be automatically communicated via computer 50 to the dispensing system 18 so that the dispensing device (not shown) can increase the dispense volume of the fillet material 22, thereby increasing fillet size. In another example, an out-of-bound measurement can trigger a process alarm that alerts the human operator that the underfill dispensing process is out-of-control so that the operation of the underfill dispensing system 18 can be manually adjusted to rectify the condition producing the out-of-bound measurement.

In another example, with corner bond dispensing, it can be desirable for material 22 to partially flow under the packaged microelectronic device 14 to form corner bonds 28 and no fillet 12, as shown in FIG. 3B. Therefore, formation of fillets 12 in this case may be deleterious. Thus, if the AOI system 19 detects the presence of fillets 12, then that is an error that is fed back to the dispensing system 18 to reduce the amount of material dispensed, or to heat up the supporting substrate 16, or both, for example, so no fillet 12 forms.

After inspection of the fillet 12, the resulting microelectronic assembly 68 may be unloaded from the AOI system 19 by suitable downstream equipment 70, such as by an automated unloader or by hand, i.e., manually. Suitable automated loaders and unloaders are available from Asymtek of Carlsbad, Calif. Next, the microelectronic assembly 68 may be manually or automatically transported to a curing device 72, such as a static oven, where the microelectronic assembly 68 with underfill material 22 is placed therein and cured, i.e., finally cross-linked to permanent form. The curing device may be included in the downstream equipment 70. After curing, the microelectronic assembly 68 can be further subjected to additional known processes and techniques, including molding processes, ball placement processes, component singulation, etc.

Accordingly, an improved system 10 and method for inspecting and controlling fillet formation is provided that overcomes the drawbacks of conventional fillet inspection systems and processes. To that end, the automated system 10 and method of the embodiments of the present invention provides fast, reliable, consistent and repeatable inspection results. Also, underfill consistency may be improved by being able to continuously adjust the operating parameters of the dispensing system 18 in real-time, without human intervention. Thus, product yield can be increased by reducing out-of-specification assemblies. And, any out-of-control situation can be quickly detected, the dispensing process stopped and/or adjusted, and either human intervention or automated adjustments relied on to correct the problem. In addition, the inspection process has improved traceability. For example, the board's serial number, its inspection result, and the login information of the operator running the inspection may be tracked. Finally, the AOI system 19 can record the size and shape of all fillets 12 on every microelectronic assembly 68 processed by the dispensing system 18.

While the present invention has been illustrated by a description of various embodiments and while these embodiments have been described in considerable detail, it is not the intention of the applicant to restrict or in any way limit the scope of the appended claims to such detail. Additional advantages and modifications will readily appear to those skilled in the art. Thus, the invention in its broader aspects is therefore not limited to the specific details, representative apparatus and method, and illustrative example shown and described. Accordingly, departures may be made from such details without departing from the spirit or scope of applicant's general inventive concept.

What is claimed is:

1. A method for use in analyzing an underfill material dispensed onto at least a first and a second supporting substrate, the method comprising:

dispensing the underfill material in a dispensing system onto the first supporting substrate adjacent to a first packaged microelectronic device attached to the first supporting substrate;

after the underfill material is dispensed, transferring the first supporting substrate, the first packaged microelectronic device, and the underfill material as an assembly from the dispensing system to an automated optical inspection system;

capturing an image of the material using the automated optical inspection system;

analyzing the image using an image-processing computer to determine one or more dimensions of a fillet formed by the underfill material at a peripheral edge or a corner of the packaged microelectronic device;

comparing the one or more dimensions of the fillet with a dimensional standard to determine whether the fillet is properly dimensioned;

communicating the one or more dimensions of the fillet from the automated optical inspection system to the dispensing system;

automatically adjusting an operating parameter of the dispensing system based upon the one or more dimensions of the fillet; and dispensing the underfill material in the dispensing system onto the second supporting substrate adjacent to a second packaged microelectronic device attached to the second supporting substrate based on the adjusted operating parameter.

2. The method of claim 1 wherein communicating the one or more dimensions of the fillet comprises:
communicating the one or more dimensions of the fillet over a feedback loop connecting a controller at the automated optical inspection system with a controller at the dispensing system.

3. The method of claim 1 wherein automatically adjusting the operating parameter comprises:
maintaining proper dimensions of the fillet.

4. The method of claim 1 further comprising:
before dispensing the underfill material, defining parameters used by the image-processing computer to determine whether the fillet is properly dimensioned.

5. The method of claim 1 wherein the fillet defines one of a no-flow underfill fillet, a corner bond fillet, an edge bond fillet, or a capillary underfill fillet.

6. The method of claim 1 wherein dispensing the underfill material in the dispensing system onto the first supporting substrate comprises:
dispensing the underfill material onto the first supporting substrate adjacent to the peripheral edge or the corner of the packaged microelectronic device.

7. An automated system for use in analyzing an underfill material dispensed onto at least a first and a second supporting substrate, the system comprising:
a dispensing system including a dispensing device configured to dispense the underfill material onto the first and second supporting substrates and adjacent to a first and second packaged microelectronic devices attached to the first and second supporting substrates, respectively;
an automated optical inspection system configured to capture an image of the underfill material dispensed onto the first support substrate and to analyze the image to determine one or more dimensions of a fillet formed by the underfill material at a peripheral edge or a corner of the first packaged microelectronic device;
a machine configured to transfer the first packaged microelectronic device, and the underfill material as an assembly from the dispensing system to the automated optical inspection system, and
a feedback loop coupling the automated optical inspection system with the dispensing system,
wherein the automated optical inspection system is configured to communicate the one or more dimensions of the fillet over the feedback loop to the dispensing system and the dispensing system is configured to dispense the underfill material onto the second supporting substrate based on the one or more dimensions of the fillet communicated to the dispensing system.

8. The system of claim 7 wherein the automated optical inspection system includes at least one camera configured to capture the image, and a controller coupled with the at least one camera, the at least one camera being adapted to communicate the image to the controller, and the controller configured to analyze the image for determining the one or more dimensions of the fillet.

9. The system of claim 7 wherein the machine comprises a conveyor sub-system adapted to convey and hold the first supporting substrate.

10. The system of claim 7 further comprising:
a loader configured for loading the packaged microelectronic device and the first supporting substrate into the dispensing system; and
an unloader configured for unloading an assembly of the first packaged microelectronic device, the first supporting substrate, and the underfill material from the automated optical inspection system.

11. The system of claim 7 further comprising:
a curing oven downstream of the automated optical inspection system, the curing oven configured for curing the underfill material.

12. The system of claim 7 wherein the dispensing system and the automated optical inspection system define an island of automation automated system.

13. The system of claim 7 wherein the dispensing system and the automated optical inspection system define an inline automated system.

14. The system of claim 7 wherein the dispensing system includes a controller coupled in communication with the dispensing device, the controller configured to supply control signals to the dispensing device for controlling the dispensing of the underfill material onto the first and second supporting substrates, and the automated optical inspection system includes a camera and a controller coupled in communication with the camera and by the feedback loop with the controller of the dispensing system, the camera configured to capture the image of the material, and the controller to analyze the image to determine one or more dimensions of the fillet.

* * * * *